(12) United States Patent
Tuntland

(10) Patent No.: US 7,605,122 B2
(45) Date of Patent: Oct. 20, 2009

(54) HUMAN CHORIONIC GONADOTROPIN (HCG) FORMULATIONS FOR FACILITATING WEIGHT LOSS AND BODY CONTOURING

(75) Inventor: Deirdre S. Tuntland, Costa Mesa, CA (US)

(73) Assignee: Millennium Medical Spa, Newport Beach, CA (US)

( * ) Notice: Subject to any disclaimer, the term of this patent is extended or adjusted under 35 U.S.C. 154(b) by 0 days.

(21) Appl. No.: 11/496,554

(22) Filed: Jul. 31, 2006

(65) Prior Publication Data

US 2007/0026027 A1    Feb. 1, 2007

Related U.S. Application Data

(60) Provisional application No. 60/704,014, filed on Jul. 29, 2005.

(51) Int. Cl.
*A61K 38/24*     (2006.01)
*C07K 14/59*    (2006.01)

(52) U.S. Cl. .......................................... 514/2; 530/399

(58) Field of Classification Search ........................ None
See application file for complete search history.

(56) References Cited

U.S. PATENT DOCUMENTS

| | | | |
|---|---|---|---|
| 5,514,670 A | 5/1996 | Friedman et al. | |
| 5,610,136 A | 3/1997 | McMichael | |
| 6,284,262 B1 * | 9/2001 | Place | 424/435 |
| 6,416,740 B1 * | 7/2002 | Unger | 424/9.52 |
| 6,720,001 B2 | 4/2004 | Chen et al. | |
| 7,101,847 B2 | 9/2006 | McMichael | |
| 2005/0096264 A1 | 5/2005 | MacDonald et al. | |
| 2006/0041058 A1 * | 2/2006 | Yin et al. | 525/50 |
| 2006/0063713 A1 * | 3/2006 | Yoon | 514/12 |
| 2008/0249302 A1 * | 10/2008 | Maddaford et al. | 540/602 |

OTHER PUBLICATIONS

"Effect of human chorionic gonadotrophin on weight loss, hunger, and feeling of well-being," W.L. Asher, M.D., and Harold W. Harper, M.D.; The American Journal of Clinical Nutrition 26: Feb. 1973, pp. 211-218.
"Controversies in Plastic Surgery: Suction-Assisted Lipectomy (SAL) and the hCG (Human Chorionic Gonadotropin) Protocol for Obesity Treatement," Trudy Vogt, M.D., and Daniel Belluscio, M.D., Aesthetic Plastic Surgery, 11:131-156, 1987.
"El Uso de la Gonadotrofina Corionica Humana (hCG) por via Oral Para el Tratamiento de la Obesidad: Estudio A Doble Ciego," Daniel O. Belluscio, M.D., and Leonor E. Ripamonte, M.D.; Rev. Inst. Med. "Sucre" LXIV: 115 (14-21) 1999.
"The Action of Chorionic Gonadotrophin in the Obese," A.T.W. Simeons, M.D. Heidelberg; The Lancet, Nov. 6, 1954, pp. 946-947.
Albrink, M.J., *Chorionic gonadotropin and obesity?*, Am J Olin Nutr, Jun. 1969, vol. 22, No. 6, pp. 681-685.
Greenway, et al., *Human chorionic gonadotropin (HCG) in the treatment of obesity: a critical assessment of the Simeons method*, West J. Med, Dec. 1977, vol. 127, No. 6, pp. 461-463.
Gusman, *Chorionic gonadotropin in obesity. Further clinical observations*, Am J Olin Nutr, Jun. 1969, vol. 22, No. 6, pp. 686-695.
Stein, et al., *Ineffectiveness of human chorionic gonadotropin in weight reduction: a double-blind study*, Am J. Clin Nutr., Sep. 1976, vol. 29, No. 9, pp. 940-948.
Veilleux, et al., *Gonadic and extragonadic effects in humans of 3,500 I.U. of HCG (human chorionic gonadotropin) in fractional doses*, Vie Med Can Fr., Sep. 1972, vol. 1, No. 9, pp. 862-871.
Boyer, *L'hCG dans l'obésité: non, non et non!*, Med Quebec, Jun. 1976, pp. 81-82.
Craig, et al., *Chorionic gonadotropin in the treatment of obese women*, Am J Clin Nutr, Mar. 1963, vol. 12, pp. 230-234.
Felig, et al., *Metabolic response to hGH during prolonged fasting*, J Clin Invest, 1971, vol. 50, pp. 411-421.
Frank, *The use of chorionic gonadotropin hormone in the treatment of obesity*, Am J Olin Hutr, 1964, vol. 14, pp. 133-136.
Berger, et al., *Is hCG therapy obesity warranted?*, Review, German, Aug. 1980, vol. 75, No. 17, pp. 624-625.
Bradley, *Human chorionic gonadotropin in weight reduction*, (letter), Am J Clin Nutr, May 1977, vol. 30, No. 5, pp. 649-654.
Hutton, *Chorionic gonadotropin and obesity*, Am J Clin Nutr, Mar. 1970, vol. 23, No. 3, pp. 243-244.
Birmingham, et al., *Human chorionic gonadotropin is of no value in the management of obesity*, Can Med Assoc J, May 15, 1983, vol. 128, pp. 1156-1157.

(Continued)

*Primary Examiner*—Marianne P Allen
*Assistant Examiner*—Regina M DeBerry
(74) *Attorney, Agent, or Firm*—Knobbe Martens Olson & Bear LLP

(57) ABSTRACT

The present invention relates to formulations of hCG for sublingual administration to mammals to facilitate weight loss and/or body contouring. Embodiments of the invention disclose administration of hCG formulations in combination with a low calorie diet and dietary supplements and, in some cases, with an exercise regime. Embodiments of this invention also disclose transdermal hCG formulations and hCG formulations for administration through other administration routes.

5 Claims, No Drawings

OTHER PUBLICATIONS

Ballin JC, White PL; Fallacy and hazard; Human chorionic gonadotropin-500-calorie diet and weight reduction; JAMA Nov. 4, 1974; 230 (5): 693-4.

Bosch B., et al., Human chorionic gonadotrophin and weight loss; A double-blind, placebo-controlled trial; S Afr Med J; Feb. 17, 1990; 77(4): 185-9.

Cairella M., Drug therapy of obesity; Clin Ter.; Mar 31, 1978; 84(6): 571-92.

Miller R., et al.; A clinical study of the use of human chorionic gonadotropin in weight reduction, J Fam Pract., Mar. 4, 1977(3): 445-8.

Rivlin RS, Therapy of obesity with hormones; N. Engl J Med; Jan 2, 1975; 292(1): 26-9.

Shetty KR, et al.; Human chorionic gonadotropin (HCG) treatment of obesity; Arch Intern Med., Feb. 1977; 137(2): 151-5.

Yanagihara Y.; Carbohydrate and lipid metabolism in pregnant albino rats during hunger after loading with gonad-stimulating hormones; Nippon Sanka Jujinka Gakkal Xasshi; Nov. 1966; 18(11): 1293-301.

Yanagihara Y.; Carbohydrate and fatty acid metabolism in pregnant albino rats simultaneously loaded with fat emulsion and sex stimulating hormones during stqarvation; Nippon Sanka Jujinka Gakkai Zasshi, Jan. 1967; 19(1): 8-14.

Yanagihara Y.; Carbohydrate and lipid metabolism in pregnant albino rats during starvation after loading with gonad-stimulating hormones; Nippon Sanka Fukinka Gakkal Zasshi, Dec. 1966; 18(12): 1379-84.

Young RL., et al., Chorionic gonadotropin in weight control. A double-blind crossover study; JAMA Nov. 29, 1976; 236(22): 2495-7.

Cargille CM: Human chorionic gonadotropin not indicated for obesity; J Am Med Assoc; 219(11): 1485-1486, 1972.

Carne S: The action of chorionic gonadotropin in the obese; Lancet II: 1282-1284, 1961.

Dunn CE: Human chorionic gonadotropin for weight reduction; Am J Obstet Gynecol; 120: 855, 1974.

Hastrup B. Nielsen B., Skouby AP: Chorionic gonadotropin and the treatment of obesity; Acta Med Scand 168(1): 25-27, 1960.

Perelberg H: Chorionic gonadotrophin (HCG) and obesity; Med J Austr 64(2): 68-69, 1977.

Bradley P; Chorionic gonadotrophin (HCG) and obesity; Med J. Aust; 22; 2(17): 581; Oct. 1977.

Bradley P; The equilibrium set-point weight; human chorionic gonadotrophin and obesity; In J. Obes. 3(4): 380-389; 1979.

Faludi G.; Use of chorionic gonadotropin in obesity; Am Fam Physician; 11(5): 156-157; May 1975.

Hutton JH, et al.; Human chorionic gonadotropin (hCG) in treatment of obesity, IMJ III Med. J; 132(5): 693-695; Nov. 1967.

Maudlin RK; Gonadotropins in obesity? Am Fam Physician; 8(4): 202-203; Oct. 1973.

Rath R., et al.; Use of choriogonadotropin in the treatment of obesity; Vnitr Leic 20(7): 681-685 Czech; Jul. 1974.

Vallini A., et al.; Treatment of obesity with chorionic gonadotropin. Relations between obesity, dyslipidemia and arthero-arteriosclerosis; Minerva Med; 7; 67(33): 2113-2132, Italian; Jul. 1976.

Simeons, M.D., Salvator Mundi International Hospital, Rome, Italy; Chorionic Gonadotropin In Geriatrics; Journal of the American Geriatrics Society, vol. IV, Jan. 1956 No. 1.

Sohar, "*A Forty-Day-550 Calorie Diet in the Treatment of Obese Outpatients*," American Journal of Clinical Nutrition, 7:514-518 (Sep.-Oct. 1959).

* cited by examiner

HUMAN CHORIONIC GONADOTROPIN (HCG) FORMULATIONS FOR FACILITATING WEIGHT LOSS AND BODY CONTOURING

CROSS REFERENCE TO RELATED APPLICATIONS

This application claims priority to and benefits from U.S. Provisional Patent Application No. 60/704,014, filed Jul. 29, 2005.

BACKGROUND OF THE INVENTION

1. Field of the Invention

This invention relates generally to formulations incorporating human chorionic gonadotropin for administration to mammals to facilitate weight loss and body contouring.

2. Description of the Related Art hCG (human chorionic gonadotrophin) is a hormone that is naturally produced during pregnancy. hCG is a glycoprotein hormone normally secreted by trophoblastic cells of the placenta during pregnancy. It consists of two chains, called the alpha and beta subunits. It is believed that one of the functions of hCG in pregnancy is to provide a constant supply of fat to the fetus regardless of what or when the mother eats. And, in particular, hCG works to supply both mother and fetus with a steady source of nutrition and fuel in the event of some kind of starvation state. For example, if the mother is ill and cannot keep food down, then hCG will break down stored fat and the baby will be born weighing approximately a normal weight (i.e. 6 or 7 lbs).

It has been postulated that there are two types of fat in the body: structural fat and excess fat. Structural fat is used by the body to provide support and fuel to vital organs. Excess fat is fat that goes directly into storage in the body. It has been found that hCG administered through injections in very small amounts in combination with a modified diet has the capability of targeting excess fat storage for use in providing support to the vital organs. Thus, hCG injections together with a modified diet result in weight loss in the areas where there is the most excess fat storage.

The beneficial effects of hCG administered by injection have been known in the medical and weight-loss industries for many years. Studies have shown that administering hCG by daily injection in small doses, e.g., 125 I.U., facilitates weight loss and redistribution of fat in human patients. See The Action of Chorionic Gonadotrophin in the Obese, A. T. W. Simeons (The Lancet, Nov. 6, 1954). Daily hCG injections administered over a period of ten days without concomitantly subjecting patients to a modified diet result in lower measurements around the hips and waists of the patients but no significant weight loss. These injections also lead to partial appetite suppression and eliminate sudden compulsive hunger experienced by some patients soon after consuming heavy meals. When combined with a modified diet, such as a very low calorie diet, the hCG injections result in significant weight loss in addition to "body contouring" (loss of excess fat in storage areas). Studies also show that this regime of hCG injections coupled with a 500 calorie/day diet does not lead to vitamin or protein deficiencies. Multiple other benefits have been observed in association with this regime. Patients that are overweight due to diabetes lose weight in response to the regime without developing acetonemia, and in cases of mild diabetes patients maintain normal blood sugar levels while weight loss is maintained; weight gain following this regime accompanied by higher sugar levels can be counteracted by another course of the regime. Following this regime, patients with gout have reduced or normal blood-uric acid levels; these patients remain well following treatment while they maintain their weight loss. Similarly, abnormally high blood-cholesterol levels decrease in patients following the regime with free cholesterol increasing and the esterified fraction decreasing, mirroring values seen in pregnancy. Treatment according to this regime also increases libido and decreases or eliminates oligomenorrhea, hyperestrogenic dysmenorrhea, fluor albus simplex, abnormal hair loss, peptic ulcer symptoms, and various dermatoses. Following the regime has also been found to cause brittle finger-nails and improve the quality of singers' voices.

However, administration of hCG by injection has created many problems for both patients and practitioners.

For patients, the process is painful and inconvenient. The injection must be given daily so patients either have to visit a clinic every day or be trained to inject themselves. Even for trained patients administering the injections can be inconvenient because the hCG solution must be refrigerated. Proper disposal of the needles and syringes is also problematic for patients and a major concern for physicians. Another potential difficulty is that in order for the injections to be effective they must be administered subcutaneously in a very specific way.

For medical practitioners, it may be hard to get consistent results depending on whether patients visit clinics daily for the injections or inject themselves properly. Another major concern is that many patients are very needle-phobic and cannot participate in an hCG program that requires the hCG to be administered by injection.

For a long period of time, medical practitioners have dealt with the drawbacks of using hCG injections because it was believed that changing the route of administration of hCG would change its biological activity such that it would not be effective for the treatment of obesity. This belief was challenged in 2003 when Dr. Daniel Belluscio of Buenos Aires, Argentina published a study on the internet suggesting that oral formulations of hCG could also be effective in promoting weight loss. See Utility of an Oral Presentation of hCG for the Management of Obesity: A Double Blind Study, Dr. Daniel Belluscio, Dr. Leonor Ripamonte, and Dr. Marcelo Wolansky (http://drbelluscio.tripod.com/hcg.htm).

There remains an unmet need in the art for oral hCG formulations and methods of administering such formulations for facilitating weight loss and body contouring as effectively as hCG injections.

SUMMARY OF THE INVENTION

Embodiments of this invention disclose sublingual formulations for promoting weight loss and/or body contouring, comprising reconstituted hCG, having a pH in the range of about 6.0 to about 8.0, one or more buffer(s), one or more absorption-enhancing compound(s), and one or more taste-enhancing agent(s). In preferred embodiments, the pH of the reconstituted hCG is about 7.0.

The buffers can be selected from the group comprising carbonates, and sodium bicarbonate is a preferred buffer. The absorption-enhancing compounds are preferably alcohols, and a highly preferred alcohol is ethanol. The one or more taste-enhancing agent(s) can be any one of the following: glycerine, monosaccharides, disaccharides, oligosaccharides, glycerol monostearate, sorbitol, mannitol, glycerol, xylitol, fructose, high fructose corn syrup, dextrose, lactose, maltose, trehalose, galactose, and artificial sweeteners. Glycerine is one preferred taste-enhancing agent. One example of an artificial sweetener to be used in some embodiments is aspartame. The sublingual hCG formulations can also comprise absorption rate enhancing compounds such as mineral oil or corn oil. In some embodiments, the formulations also comprise one or more flavored syrup(s). Different forms of the hCG formulations include a liquid, tablet, lozenge, capsule, or spray.

Embodiments of this invention also disclose methods of reducing body weight and/or contouring the body of a patient comprising administering hCG formulations to patients sublingually. The formulations can, for example, be administered twice daily, in doses of 0.125 ml per administration. In some embodiments, the formulations can be held sublingually by patients for between about 30 seconds and about 45 seconds. The hCG formulations can also be administered in combination with modified diets. For example, patients can be put on a low calorie diet, sometimes comprising between about 500 and about 700 calories per day. The diet may also include pharmacological support such as appetite suppressants and potassium supplements. In some embodiments, the hCG patients are further subjected to an exercise regime.

The rate of absorption of sublingual hCG formulations can be determined by administering embodiments of the formulations comprising flavored syrup(s).

Embodiments of this invention also disclose transdermal formulations for promoting weight loss and/or body contouring, comprising reconstituted hCG and one or more absorption-enhancing agent(s). The absorption-enhancing agent(s) can comprise liposomes, dermal penetration enhancers, and lipophilic solvents and formulations. The transdermal formulations can be in the form of a cream, lotion, spray, solution, or skin patch. The transdermal formulations can also comprise ointment bases such as hydrophilic ointments or a petrolatum bases.

Embodiments of this invention also disclose methods of reducing body weight and/or contouring the body of a patient comprising administering hCG formulations as described above transdermally. Furthermore, hCG formulations can be administered transdermally in combination with subjecting patients to ultrasound.

The sublingual and transdermal hCG formulations can, in some embodiments, comprise viscosity-increasing agents such as methylcellulose.

DETAILED DESCRIPTION OF THE PREFERRED EMBODIMENT

Embodiments of the present invention disclose novel formulations of hCG and novel methods of administering hCG formulations to facilitate weight loss and/or body contouring.

In some embodiments hCG is formulated for oral sublingual administration. Recent studies have suggested that hCG may be effective in producing weight loss when administered orally. See Utility of an Oral Presentation of hCG for the Management of Obesity: A Double Blind Study, Dr. Daniel Belluscio, Dr. Leonor Ripamonte, and Dr. Marcelo Wolansky (http://drbelluscio.tripod.com/hcg.htm).

The prior art has not addressed the problem of formulating hCG such that it can be sufficiently absorbed to achieve desired weight loss and body contouring results. Embodiments of the present invention disclose oral hCG formulations and other hCG formulations with enhanced absorbability.

hCG may be purchased from the manufacturer in a lyophilized freeze-dried state together with bacteriostatic (sterile) water for reconstitution. Reconstitution is a process to bring a liquid concentrate or powder form to normal strength by adding water. Once the hCG is reconstituted with sterile water, it must be stored in a liquid form. In this liquid state, the hCG formulation must be refrigerated.

The absorbability of hCG formulations can be enhanced by adjusting the pH of the formulations. In one preferred embodiment, hCG is formulated for oral sublingual administration. Experiments have shown that a pH close to 7.0 results in an optimal level of sublingual absorption. In order to achieve optimal absorption of hCG through the mucous membranes and vasculature found under the tongue, the pH of reconstituted hCG is adjusted to fall approximately within the range of 6.0 to 8.0. In a preferred embodiment the pH of reconstituted hCG is adjusted to about 7.0. An hCG formulation that can be absorbed sublingually is desirable because the formulation is absorbed by the vasculature under the tongue and thus taken up directly by the bloodstream. The pH of reconstituted hCG can also be adjusted to different values depending on where in the body a formulation is to be absorbed, as would be understood by those skilled in the art. The pH of reconstituted hCG can be adjusted, for example, by combining it with a buffer(s). In some embodiments of the present invention, formulations of hCG for oral sublingual administration are made by combining reconstituted hCG with a buffer(s) and then refrigerating the combination. In preferred embodiments the buffer(s) added to the reconstituted hCG may be selected from the group consisting of the carbonates. In more preferred embodiments, the reconstituted hCG is combined with sodium bicarbonate. The biocompatibility and easy accessibility of sodium bicarbonate make it a preferred choice for a buffer. The buffer(s) can be any compound that adjusts the pH of the reconstituted hCG without negatively affecting its suitability for consumption. Any other means may be used to adjust the pH of the hCG formulations as would be contemplated by those skilled in the art.

The absorbability of hCG at various anatomical locations can also be enhanced by combining it with one or more absorption-enhancing compounds. In preferred embodiments, one or more alcohols are included in an hCG formulation to enhance its absorption. In highly preferred embodiments, the hCG formulation comprises ethanol. Addition of a compound(s) to enhance absorption allows the administration of smaller doses of hCG formulation to achieve similar results to those achieved with the higher doses required when no absorption-enhancing compound is included. For example, in embodiments of the invention in which an hCG formulation for sublingual administration comprises an absorption-enhancing compound(s), the formulation may be absorbed when retained sublingually for less than 30 seconds. In some embodiments of the invention in which an hCG formulation for sublingual administration comprises an absorption-enhancing compound(s), the formulation may be absorbed when retained sublingually for less than 20 seconds. In some embodiments, a lipid-soluble vehicle, such as mineral oil or corn oil, can also be included in an hCG formulation to increase its absorption rate. Different flavored syrups can be added to the hCG formulations with the flavor of the syrups lasting until the hCG has been absorbed. This can aid in determining the rate of hCG absorption.

In some embodiments, taste-enhancing compound(s) suitable for consumption can be added to an hCG formulation. For example, the taste-enhancing compounds may make the formulation sweeter, saltier, more sour, less bitter, more neutral in taste, or otherwise more palatable to patients, depending on the particular patient. In preferred embodiments, the taste-enhancing compounds render the hCG formulation sweeter. In more preferred embodiments, the taste-enhancing compound is selected from the group comprising glycerine, monosaccharides, disaccharides, oligosaccharides, glycerol monostearate, sorbitol, mannitol, glycerol, xylitol, fructose, high fructose corn syrup, dextrose, lactose, maltose, trehalose, galactose, and artificial sweeteners, including aspartame. In a highly preferred embodiment, the hCG formulation comprises glycerine to render the formulation slightly sweet without adding any artificial flavor.

In a preferred embodiment, hCG is formulated for sublingual administration and comprises reconstituted hCG with a pH in the range of 6.0 to 8.0, one or more buffer(s), one or more absorption-enhancing compound(s), and one or more taste-enhancing compound(s). In a more preferred embodiment hCG is formulated for sublingual administration and comprises reconstituted hCG with a pH of about 7.0, sodium bicarbonate, ethanol, and glycerine. In a most preferred embodiment, the hCG formulation for sublingual administration includes 10,000 USP units in 10 ml of reconstituted lyophilized hCG, 1 ml sodium bicarbonate, 4 ml glycerin, and ethanol (total 5%—usually between about 0.5-5 ml). In some embodiments, the sublingual hCG formulation can be used for up to 60 days if refrigerated.

In some embodiments an hCG formulation for sublingual administration may be absorbed when retained sublingually for about two minutes. In more preferred embodiments, an hCG formulation for sublingual administration may be absorbed when retained sublingually for about one minute. In a most preferred embodiment, an hCG formulation for sublingual administration may be absorbed when retained sublingually for about 30 to 45 seconds. In some embodiments an hCG formulation for sublingual administration may be absorbed when retained sublingually for less than 30 seconds.

In some embodiments, hCG can be formulated for sublingual administration as a tablet, lozenge, spray, or liquid capsule. For example, a liquid tablet could comprise a coating that dissolves upon contact with the sublingual area of the mouth such that the liquid within the tablet can subsequently be absorbed.

In some embodiments, hCG can be administered transdermally such that it is released within patients' bodies for particular durations of time in a uniform manner or in other pre-determined patterns depending on the individual needs of patients. For example, hCG can be formulated as a cream, lotion, spray, solution, skin patch, or in any other form for transdermal administration as would be understood by those skilled in the art. Embodiments of transdermal formulations can include ointment bases such as hydrophilic ointments or petrolatum bases. Conventional skin absorption technologies, e.g., liposomes, dermal penetration enhancers, ultrasound, and lipophilic solvents and formulations may be used in transdermal hCG formulations to provide adequate dosing. Those of skill in the art will be able to optimize the transdermal dosing for producing desired weight loss and/or body contouring results.

In some embodiments, viscosity-increasing agents such as methylcellulose can be added to either sublingual or transdermal hCG formulations to create gels.

In some embodiments, an hCG formulation is combined with behavior modification, e.g., exercise, weight training, yoga, sleep changes, smoking cessation, and/or pharmacologic support, e.g., diet suppressants, vitamins and mineral supplements, and/or specific dietary guidelines, e.g., calorie intake, that do not conflict with and that may promote the weight loss and body contouring associated with hCG administration. In some embodiments, the pharmacologic support includes compound(s) selected from the group comprising appetite suppressants, diuretics, and potassium supplements.

In some preferred embodiments an hCG formulation is administered in combination with a very low calorie diet (VLCD). In one preferred embodiment, 0.125 ml of an hCG formulation is administered sublingually twice a day (once in the morning, once in the evening) in combination with a daily diet of between about 500 and about 700 calories which may include low or no calorie fluids, lean meats and fish and other proteins, certain vegetables and fruits, small portions of particular carbohydrates, artificial sweeteners, seasonings, and water. The hCG formulation can, in preferred embodiments, be absorbed after being held under the tongue for 30 to 45 seconds. In some embodiments, 0.250 ml of an hCG formulation is administered sublingually twice a day. In preferred embodiments the only fluids allowed are tea, coffee, mineral water, soda water, and two cans of diet soda per day, 2 liters of water are consumed per day, and lunch and dinner each comprise 3.5 ounces (weighed raw) of lean meat such as veal, steak, fresh white fish (bass, flounder, pike, brooke trout, jew fish, john dory, flathead, bream, or snapper), chicken without skin, or fresh shell fish (oysters, clams, mussels, prawns, crab meat, lobster, or scallops), 3.5 ounces of vegetables such as green beans, spinach, brussel sprouts, lettuce, radish, tomatoes, cucumber, mushrooms, celery, fresh asparagus, capsicum, onion, zucchini, bean shoots, or cabbage, two servings of fruit (one serving=1 apple, 6 strawberries, 1 orange, or ½ grapefruit) per day consumed 6 hours apart, and two servings of carbohydrates (one serving=1 Ryvita or Ry Krisp, 1 slice of bread) per day consumed 6 hours apart. In preferred embodiments the lean meats chosen for lunch and dinner are selected from the group comprising veal and fresh fish and are cooked after all visible fat has been removed and without any additional fat. In preferred embodiments, the juice of one lemon, one tablespoon of milk, one tablespoon of low calorie and non-fat French dressing, and any amount of artificial sweetener, salt, pepper, vinegar, and other spices are allowed, no margarine, butter, oil, oil-based dressings, or malt vinegar are allowed, and the daily diet includes a prescription appetite suppressant and a potassium supplement. Other example diets are provided infra. Other diets, such as low carbohydrate, low fat, and high protein diets, commercial diets, and any other diets and nutrition plans can also be used in combination with administering hCG, depending on particular patient needs as would be understood by those skilled in the art. In some embodiments, the diet combined with administration of the hCG formulation includes items that may be chosen at various restaurants.

In some embodiments, hCG can be formulated to be administered to animals, particularly other mammals, to facilitate weight loss and/or body contouring.

In some embodiments administration of hCG combined with a diet plan is also combined with an exercise regime, e.g., 30 to 45 minutes of walking, swimming, or other cardiovascular exercise 3 times per week for 1 hr, and/or low impact exercise or other exercise regimens as would be contemplated by those skilled in the art, including weight training, yoga, pilates, aerobics, etc., depending on the needs of individual patients.

One skilled in the art will understand that a patient's diet in combination with administration of hCG formulations can be modified in multiple other ways depending on the individual needs of the patient. For example, patients may follow a diet comprising a wide range of number of calories per day, fewer or greater than three meals per day, and a variety of food items depending on the patients' health and other needs. The fat, protein, carbohydrate, and other constituent percentages of patients' diets may also be varied and modified according to patients' particular needs.

In a preferred embodiment the oral hCG formulation is administered twice daily in combination with a diet of between about 500 calories and about 700 calories per day. In a most preferred embodiment the oral hCG formulation is administered twice daily, once in the morning, once in the evening, in amounts of 0.125 ml placed under the tongue for 30 to 45 seconds in combination with a diet of between about 500 calories and about 700 calories per day and a prescription appetite suppressant and a potassium supplement.

In some embodiments, the hCG formulations may be administered alone without restricting patients' diets. Administration of hCG without modifications to patients' diets or other behavior may result in body contouring without weight loss. In other embodiments, the hCG formulations may be administered without restricting patients' diets for a few days.

In some embodiments, in addition to the oral hCG and diet plan, patients undergo an initial consultation and brief physical examination, weight and height measurements and photos are taken, medical history is noted, and patients are screened for medications and allergies to medications. Patients may also be given a thorough explanation of how the program works as well as specific instructions on how to take the medications and use the oral hCG. Patients will be placed on an oral hCG and diet regime, possibly including exercise, based on their specific needs, determined partly based on the initial consultation, measurements, and the patients' medical needs. Following a 1 week long course of the oral hCG and diet plan regime per aspects of this invention, patients undergo another consultation, weight measurements and photos are retaken, and any other indications of responses to the regime are noted. Additional courses of the regime may then be administered depending on the needs of particular patients.

Various methods of measuring weight loss and changes in body contour and subcutaneous fat are disclosed per embodiments of this invention. Skinfold thickness (SKF) and Tetrapolar Bioelectric Impedance (TBI) measurements of patients can be taken. Both approaches have been extensively discussed in the literature. It has been shown that the correlation between the values obtained with the two methods is linear and highly significant for both sexes. There is general agreement in the art that skinfold calipers are useful in the clinical setting particularly because measurements of subcutaneous body fat at different body sites is becoming increasingly important for assessing the risk of certain disease states such as diabetes, syndrome X, and heart disease.

Body circumference estimates can be used to determine changes in body contour following hCG administration. Although some data suggests that body circumference estimates may be more accurate in determining subcutaneous body fat than SKF assessments, clinical variables such as bloating and water retention may render body fat assessments less accurate than SKF assessments. Also, when comparing SKF and body circumference estimates, some data suggests that the pattern of fat thickness body distribution measured over several specific sites by one method of measurement is unlikely to be duplicated by the other method on the same individual.

Adipose tissue patterns show great variability, indicating the importance of using skinfold caliper readings from a variety of different anatomic sites including upper limbs, lower limbs, and trunk. Studies show that specific SKF areas such as the upper and lower umbilical areas are highly responsive to hCG pharmacological intervention. Greater response is observed in those regions where the corresponding circumference assessments result in significant decreases.

The formulations of hCG as disclosed in embodiments of this invention, in particular the sublingual formulations, are as effective in achieving body contouring as hCG administered by injection, and when combined with modified diets as discussed above these formulations are also as effective as hCG injections in achieving weight loss. Furthermore, the oral sublingual and other formulations of hCG disclosed herein are far more convenient and appealing to patients than the hCG injections known in the prior art. The hCG formulations disclosed per aspects of this invention provide great advantages over previous routes of administration. Patients can take the formulations with them and more easily comply with administration regimes. Patients do not need to be trained on how to use or dispose of these formulations, and are more likely to follow the administration regimes because they can administer the formulations every day without significantly inconveniencing themselves. The formulations are also appealing alternatives to hCG injections for patients who are needle-phobic.

The benefits associated with the hCG formulations discussed above have motivated many patients to switch from hCG injections to sublingual hCG formulations and to inform other hCG users and other people interested in weight loss and body contouring of these benefits. Other benefits associated with the formulations have been touted by patients following a regime of sublingual hCG formulation combined with a VLCD per embodiments of this invention. These patients have lost an average of about 4 to about 15 pounds per week over a period of 8 weeks and have noted the tremendous levels of energy they experienced during the regime, how easy the regime is to follow, and the rapid loss of weight that they are able to keep off. They have also remarked on the superiority of the regime as compared to other weight loss programs. Some patients who have tried many weight loss programs in the past have claimed that the regime is the only weight loss program that worked for them. Thus many more potential patients continue to become interested in the weight loss regimes disclosed in embodiments of this invention. Studies have also shown that oral administration of hCG is safe and does not cause undesirable side effects.

hCG weight loss programs are associated not only with weight loss but with significant changes in subcutaneous fat stores and body contouring that results form loss of excess fat from fat storage areas of the body. In particular, oral administration of hCG has been found to decrease specific body circumstances and SKF from fat storage areas.

Studies have also shown that patients taking hCG have a greater ability to handle irritability that may be caused by a low calorie diet, are less prone to experiencing extreme nervousness, improved in their sense of well-being and in their mood, and less fatigued.

Prior Art Example

In the following example, a double-blind study of 70 female patients was conducted in which the patients were administered either sublingual formulations of hCG or a placebo in combination with a modified diet. See Utility of an Oral Presentation of hCG for the Management of Obesity: A Double Blind Study, Dr. Daniel Belluscio, Dr. Leonor Ripamonte, and Dr. Marcelo Wolansky (http://drbelluscio.tripod.com/hcg.htm). The patients studied were at least 25% BMI (Body Mass Index) overweight, and in generally healthy condition. If taking medication for obesity, such as anorectics or amphetamines, they discontinued the medication at least one month prior the initiation of the study. Drugs to control clinical diseases, such as hypertension, hypothyroidism, etc., were allowed. No patients taking steroids, diuretics or hormones were entered in the study. No patients with severe and/or uncontrolled clinical diseases such as cancer, IDDM, heart attacks, and infarcts sequelae were accepted. The patients were assigned to groups Placebo (P, N=26) or hCG (N=44) by a simple randomized sampling method. The latter group was in turn split into two subgroups: G1 (N=36) and G2 (N=8), according to the hCG dose administered (see below).

All these patients were Caucasian ranging from 23 to 73 years of age (group P: 41±13; group G1: 42±12; group G2: 41±14), from 1.62 m to 1.81 m in height, and from 25 to 49.9 on BMI Tables.

Group G2 was administered twice the hCG dose of group G1 to assess if hCG concentration may affect obtained results. The placebo vials contained saline solution (NaCl 0.9% w/v), and the hCG formulation vials contained diluted and buffered solutions of standardized hCG.

The same VLCD was prescribed to all groups, as follows:

Breakfast: tea or coffee in any quantity without sugar (one tablespoonful of milk allowed in a 24-hour period; saccharin or other sweeteners allowed).

Lunch: (1) 100 grams of veal, beef, chicken breast, fresh white fish, lobster, crab or shrimp (all visible fat carefully removed before cooking, and the meat weighed raw; salmon, tuna fish, herring, dried or pickled fish not allowed; chicken breast removed raw from the bird). (2) One type of vegetable chosen from the following: spinach, chard, chicory, beet-greens, green salad, tomatoes, celery, fennel, onions, red radishes, cucumbers, asparagus, and cabbage. (3) One breadstick (grissini) or one Melba toast, and (4) an apple or an orange, or a handful of strawberries or one-half grapefruit.

For dinner: The same four choices as lunch.

The juice of only one lemon daily was allowed for all purposes. Salt, pepper, vinegar, mustard power, garlic, sweet basil, parsley, thyme, marjoram, etc., could be used for seasoning, but no oil, butter or dressing were allowed. Tea, coffee, plain water, and mineral water were the only drinks allowed, but they could be taken in any quantity and at all times.

The following evaluations were completed once a week:

I. Height and Weight, performed on a medical scale.

II. Body circumferences, using a flexible, non elastic metric tape. The following anatomic areas were assessed:

Wrist (WRT), at the level of flexion fold (wrist-forearm);
Breast (BRE), submammary fold;
Waist (WAT), at the hypogastric region level;
Abdominal (ABD), at the navel level;
Hips (HIP), pubic line;
Thighs (THI), 8 cm. below pubic line;
Suprapatelar (ROT), at the patella upper border;
Ankle (ANK), at the flexion fold (peroneal protuberance).

III. Skinfold thickness, using a Lange Skinfold Caliper (Cambridge Scientific Industries, Cambridge, Md.). The following folds were examined:

Tricipital (TRI), arm midline, posterior region and tricipital muscle zone;
Anterior Axilar line (AXA), at the fold created when pinching the skin region at the level of the pectoralis muscle extending to the arm;
Subscapular (SCA (I)), inferior scapular spine;
Thoracic (TOR), at the fold created when pinching the region located immediately below the ribs, at the level of an imaginary line extending from anterior axilar line;
Suprailiac (ILI), at the fold created 4 cm above the anterior superior iliac spine;
Supraumbilical (UMB(u)), 3 cm above navel;
Infraumbilical (UMB(l)), 3 cm below navel;
Thighs (THI), internal aspect of thighs, eight cm below the pubic area;
Patellar area (ROT), at the fold created when pinching the region located 6 cm medial to the internal patellar border.

IV. Bioelectrical impedance, using Tetrapolar Bioelectrical Impedance (TBI) with a body fat analyzer Maltron, model BF-905 (Maltron International Ltd., Rayleigh, Essex).

Volunteers were suggested to void, placed on supine position thereafter, and allowed to rest half an hour before determination. Self-adhering electrodes were placed on extremities. Every determination was performed with a separate set of electrodes that were discarded after single use.

The following TBI determinations were assessed:
1. Fat weight (FW),
2. Lean weight (LW),
3. Water weight (WW),
4. Calories (CAL).

V. b-hCG determinations. All subjects enrolled in the trial were studied for plasmatic b-hCG levels by an ELISA test (64) on 0-15-30 study days.

VI. Mood questionnaire. From the first study week on, patients were given weekly self-administered questionnaires to be completed at home. It consisted of twenty-four questions related to their mood changes in the course of the study, plus four questions related to adverse drug effects. They returned the data at the time of the subsequent visit to the clinic.

Variables were categorized as follows for a better data processing and statistical results presentation:

Category I. BW (body weight) plus four bioelectrical impedance records (FW, LW, WW and CAL).

Category II. Eight anthropometrical measurements (corporal circumferences WRT, BRE, WAT, ABD, HIP, THI, ROT and ANK).

Category III. Nine skinfold assessments (TRI, AXA, SCA (I), TOR, ILI, UMB(u), UMB(l), THI, ROT) (see long names and definitions for the studied variables at the beginning of this section).

Plasma hCG remained undetectable both in placebo and hCG groups throughout the prior art study of Belluscio et al. Moreover, the oral administration of hCG did not result in a significant change in weight loss. Treatment did however result in some therapeutic advantages.

hCG-treated groups were more capable of handling their irritability and their moods at home, and were less prone to episodes of extreme nervousness resulting in violent discussions. Several reports proposed hCG might be used for the treatment of psychoses or neurosis.

It is well known that VLCDs are associated with mood changes, particularly attrition during the dieting period. In one study, disinhibition and hunger were significantly related to anxiety and depression while restraint was not. Another study concluded that elevated levels of anxiety persist in female patients throughout a VLCD course of treatment.

Also many patients typically complain about fatigue in the course of a VLCD.

Data from the Belluscio study suggests that hCG-treated volunteers improved their attitude towards their environment, in the sense of an enhanced sense of well-being, less irritability and lack of fatigue. Since commercial preparations of hCG contains b-endorphin and this neuropeptide has been demonstrated to affect the function of limbic-emotional circuits, the b-endorphin fraction present in commercial preparations of hCG might account for the activity observed regarding mood control.

The combination of a VLCD and oral hCG formulation could trigger clinically significant changes in subcutaneous fat stores and simultaneously decrease body weight and modulate body contour.

Working Example

In Applicant's studies, modification of the hCG formulation from the basic reconstituted hCG used in the Belluscio study, to include pH adjustment to about 7.0 and addition of an absorption enhancing agent (e.g., ethanol) have resulted in surprising and unexpected weight loss and body contouring.

The hCG formulation for sublingual administration in the WORKING EXAMPLE comprises 10,000 USP units in 10 ml of reconstituted lyophilized hCG, 1 ml sodium bicarbonate, 4 ml glycerin, and ethanol (total 5%)—adjusted to pH 7. In one group of patients (Low dose), doses of 0.125 ml of the above hCG formulation was administered sublingually twice a day (once in the morning, once in the evening) in combination with a VLCD daily diet (similar to that used by Belluscio) of between about 500 and about 700 calories comprising low or no calorie fluids, lean meats and fish and other proteins, vegetables and fruits, small portions of carbohydrates, artificial sweeteners, seasonings, and water. The hCG formulation was administered orally and held under the tongue for 30 to 45 seconds.

Average weight loss per week in the Low dose group was as follows: Week 1—8.9 lbs; Week 2—6.9 lbs; Week 3—6.4 lbs; Week 4—14.8 lbs; Week 5—7.4 lbs; Week 6—4 lbs; Week 7—5.96 lbs; and Week 8—5.7 lbs. Thus, Applicant's formulation and weight loss regimen was unexpectedly found to be much more effective than Belluscio's published study.

What is claimed is:

1. A sublingual formulation of hCG for promoting weight loss in a human on a reduced calorie diet, comprising:
   reconstituted hCG, in an amount sufficient to promote weight loss in said human when the formulation is administered sublingually;
   a pharmaceutically acceptable buffer consisting of sodium bicarbonate in an amount sufficient to adjust the pH of the formulation to a range of about 7 to about 8;
   a taste-enhancing agent consisting of glycerin; and
   an absorption-enhancing compound consisting of ethanol.

2. The formulation of claim 1, further comprising an absorption rate enhancing compound.

3. The formulation of claim 2, wherein the absorption rate enhancing compound is selected from the group consisting of mineral oil and corn oil.

4. The formulation of claim 1, further comprising one or more flavored syrup(s).

5. The formulation of claim 1, wherein the formulation is in the form of a liquid, tablet, lozenge, capsule, or spray.

* * * * *

UNITED STATES PATENT AND TRADEMARK OFFICE
CERTIFICATE OF CORRECTION

PATENT NO. : 7,605,122 B2  Page 1 of 1
APPLICATION NO. : 11/496554
DATED : October 20, 2009
INVENTOR(S) : Deirdre S. Tuntland It is certified that error appears in the above-identified patent and that said Letters Patent is hereby corrected as shown below:

Title page, Item (56), Column 2, Line 7, under Other Publications, change "Olin" to --Clin--.

Title page, Item (56), Column 2, Line 13, under Other Publications, change "Olin" to --Clin--.

Title page, Item (56), Column 2, Line 27, under Other Publications, change "Olin Hutr" to --Clin Nutr--.

Signed and Sealed this

Twenty-third Day of March, 2010

David J. Kappos
*Director of the United States Patent and Trademark Office*